United States Patent
Averina et al.

(10) Patent No.: US 10,596,381 B2
(45) Date of Patent: Mar. 24, 2020

(54) PHYSIOLOGIC RESPONSE TO POSTURE

(75) Inventors: Viktoria A. Averina, Roseville, MN (US); John D. Hatlestad, Maplewood, MN (US); Abhilash Patangay, Inver Grove Heights, MN (US); Pramodsingh Hirasingh Thakur, White Bear Lake, MN (US); Yi Zhang, Plymouth, MN (US); Kenneth C. Beck, Liberty, UT (US)

(73) Assignee: Cardiac Pacemakers, Inc., St. Paul, MN (US)

(*) Notice: Subject to any disclaimer, the term of this patent is extended or adjusted under 35 U.S.C. 154(b) by 711 days.

(21) Appl. No.: 13/325,354

(22) Filed: Dec. 14, 2011

(65) Prior Publication Data

US 2012/0157798 A1 Jun. 21, 2012

Related U.S. Application Data

(60) Provisional application No. 61/425,066, filed on Dec. 20, 2010.

(51) Int. Cl.
*A61B 5/11* (2006.01)
*A61B 5/053* (2006.01)
(Continued)

(52) U.S. Cl.
CPC ........ *A61N 1/36542* (2013.01); *A61B 5/0205* (2013.01); *A61B 5/0538* (2013.01);
(Continued)

(58) Field of Classification Search
CPC ........ A61B 5/0245; A61B 5/1116; A61N 1/37
(Continued)

(56) References Cited

U.S. PATENT DOCUMENTS 5,472,453 A 12/1995 Alt
5,593,431 A 1/1997 Sheldon
(Continued)

FOREIGN PATENT DOCUMENTS

JP 2014502535 A 2/2014
WO WO-2010014497 A1 2/2010
(Continued)

OTHER PUBLICATIONS

Vanderheyden, Marc, et al., "Continuous Monitoring of Intrathoracic Impedance and Right Ventricular Pressures in Patients with Heart Failure", Circulation: Heart Failure, (Mar. 2010), 29 pgs.
(Continued)

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

An implantable or other ambulatory medical apparatus comprises a posture sensing circuit, a physiologic sensing circuit that senses a time varying physiologic signal, and a processor circuit. The processor circuit includes a posture calculation circuit and a measurement circuit. The posture calculation circuit determines a posture of the subject using posture data obtained using the posture signal and determines when the posture of the subject is steady state. The measurement circuit derives a physiologic measurement using physiologic data extracted from the physiologic signal during at least one time period when posture is determined to be steady state and provides the physiologic measurement to at least one of a user and a process in association with the determined steady state posture.

16 Claims, 5 Drawing Sheets

(51) Int. Cl.
*A61N 1/365* (2006.01)
*A61B 5/0205* (2006.01)
*A61B 5/00* (2006.01)
*A61B 5/08* (2006.01)
*A61B 7/04* (2006.01)

(52) U.S. Cl.
CPC .......... *A61B 5/1116* (2013.01); *A61B 5/6869* (2013.01); *A61B 5/0809* (2013.01); *A61B 5/686* (2013.01); *A61B 7/04* (2013.01)

(58) Field of Classification Search
USPC .......................... 607/28; 600/510, 483, 484
See application file for complete search history.

(56) References Cited

U.S. PATENT DOCUMENTS

| | | | |
|---|---|---|---|
| 5,957,957 A | 9/1999 | Sheldon | |
| 6,044,297 A | 3/2000 | Sheldon et al. | |
| 6,076,015 A | 6/2000 | Hartley et al. | |
| 6,408,208 B1 | 6/2002 | Sun | |
| 6,438,408 B1 | 8/2002 | Mulligan et al. | |
| 6,666,826 B2 | 12/2003 | Salo et al. | |
| 6,719,701 B2 | 4/2004 | Lade | |
| 6,738,667 B2 | 5/2004 | Deno et al. | |
| 6,751,503 B1 | 6/2004 | Kroll | |
| 6,829,507 B1 | 12/2004 | Lidman et al. | |
| 6,949,075 B2 | 9/2005 | Hatlestad et al. | |
| 6,975,904 B1* | 12/2005 | Sloman | 607/28 |
| 7,149,579 B1 | 12/2006 | Koh et al. | |
| 7,149,584 B1 | 12/2006 | Koh et al. | |
| 7,171,270 B1 | 1/2007 | Park et al. | |
| 7,313,440 B2 | 12/2007 | Miesel | |
| 7,330,760 B2 | 2/2008 | Heruth et al. | |
| 7,336,999 B1 | 2/2008 | Koh | |
| 7,340,296 B2 | 3/2008 | Stahmann et al. | |
| 7,400,928 B2 | 7/2008 | Hatlestad | |
| 7,447,545 B2 | 11/2008 | Heruth et al. | |
| 7,471,290 B2 | 12/2008 | Wang | |
| 7,559,901 B2 | 7/2009 | Maile et al. | |
| 7,578,794 B2 | 8/2009 | Hatlestad et al. | |
| 7,578,795 B2 | 8/2009 | Hu et al. | |
| 7,599,741 B2 | 10/2009 | Hopper et al. | |
| 7,636,599 B1 | 12/2009 | Koh et al. | |
| 7,647,106 B2 | 1/2010 | Virag et al. | |
| 7,662,104 B2 | 2/2010 | Krzysztof et al. | |
| 7,664,546 B2 | 2/2010 | Hartley et al. | |
| 7,805,185 B2 | 9/2010 | Zhang et al. | |
| 7,951,087 B2 | 5/2011 | Siejko et al. | |
| 8,012,098 B2 | 9/2011 | Maile et al. | |
| 2004/0127792 A1 | 7/2004 | Siejko et al. | |
| 2005/0209645 A1* | 9/2005 | Heruth et al. | 607/3 |
| 2005/0245988 A1 | 11/2005 | Miesel | |
| 2006/0015149 A1 | 1/2006 | Baker | |
| 2006/0036290 A1 | 2/2006 | Hopper et al. | |
| 2006/0253043 A1 | 11/2006 | Zhang et al. | |
| 2007/0021678 A1* | 1/2007 | Beck et al. | 600/510 |
| 2007/0118056 A1 | 5/2007 | Wang et al. | |
| 2007/0129641 A1 | 6/2007 | Sweeney | |
| 2007/0129643 A1 | 6/2007 | Kwok et al. | |
| 2007/0142868 A1 | 6/2007 | Moon et al. | |
| 2007/0161912 A1 | 7/2007 | Zhang | |
| 2007/0191904 A1 | 8/2007 | Libbus et al. | |
| 2008/0004664 A1 | 1/2008 | Hopper et al. | |
| 2008/0033304 A1 | 2/2008 | Dalal et al. | |
| 2008/0082001 A1 | 4/2008 | Hatlestad et al. | |
| 2008/0108907 A1 | 5/2008 | Stahmann et al. | |
| 2008/0262360 A1 | 10/2008 | Dalal et al. | |
| 2008/0269622 A1 | 10/2008 | Hatlestad | |
| 2009/0024005 A1 | 1/2009 | Lewicke et al. | |
| 2009/0312815 A1 | 12/2009 | Hopper et al. | |
| 2009/0312973 A1 | 12/2009 | Hatlestad et al. | |
| 2010/0010378 A1 | 1/2010 | Hatlestad et al. | |
| 2010/0030090 A1 | 2/2010 | Zhang et al. | |

FOREIGN PATENT DOCUMENTS

| | | |
|---|---|---|
| WO | WO-2012087696 A2 | 6/2012 |
| WO | WO-2012087696 A3 | 6/2012 |

OTHER PUBLICATIONS

"International Application Serial No. PCT/US2011/064811, International Preliminary Report on Patentability dated Jul. 4, 2013", 12 pgs.

"International Application Serial No. PCT/US2011/064811, International Search Report dated Jun. 18, 2012", 7 pgs.

"International Application Serial No. PCT/US2011/064811, Written Opinion dated Jun. 18, 2012", 10 pgs.

* cited by examiner

PHYSIOLOGIC RESPONSE TO POSTURE

CROSS-REFERENCE TO RELATED APPLICATIONS

This application claims the benefit of U.S. Provisional Application No. 61/425,066, filed on Dec. 20, 2010, under 35 U.S.C. § 119(e), which is incorporated herein by reference in its entirety.

BACKGROUND

Medical devices can include devices designed to be implanted into a patient. Some examples of these implantable medical devices (IMDs) include cardiac function management (CFM) devices such as implantable pacemakers, implantable cardioverter defibrillators (ICDs), and cardiac resynchronization therapy devices (CRTs). The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices can also include wearable medical devices (WMDs) such as wearable cardioverter defibrillators (WCDs) and wearable diagnostic devices. WCDs are monitors that include surface electrodes. The surface electrodes are arranged to provide one or both of monitoring surface electrocardiograms (ECGs) and delivering cardioverter and defibrillator shock therapy. Medical devices can of course also be stationary devices to provide diagnostic capability and therapy to bedridden or otherwise less mobile patients.

Some medical devices include one or more sensors to monitor different physiologic aspects of the patient. Patient posture can be sensed with a posture sensor. Sensing of patient posture can provide information related to a patient's condition or disease. For example, a patient with congestive heart failure (CHF) may tend to sleep in an upward position as their condition worsens. Patient posture information may also be useful in other aspects of patient monitoring. For example, physiologic measurements taken by a medical device may vary with patient posture. Knowledge of the posture of the patient during the measurements may be useful to a caregiver in interpreting the device-based measurements.

OVERVIEW

This document relates generally to systems, devices, and methods for determining posture in a patient or subject. In particular it relates to systems, devices, and methods for monitoring one or more physiologic aspects of a patient or subject in association with posture of the patient or subject.

In an example, an apparatus includes a posture sensing circuit, a physiologic sensing circuit that senses one or more time varying physiologic signals, and a processor circuit. The processor circuit includes a posture calculation circuit and a measurement circuit. The posture calculation circuit determines a posture of the subject using posture data obtained using the posture signal and determines when the posture of the subject is substantially steady state, or relatively invariant in time. The measurement circuit derives a physiologic measurement using physiologic data extracted from the physiologic signal during at least one time period when posture is determined to be steady state and provides the physiologic measurement to at least one of a user and a process in association with the determined steady state posture.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

A medical device (e.g., ambulatory, such an IMD or WMD, or stationary) can include one or more of the features, structures, methods, or combinations thereof described herein. For example, a cardiac monitor or a cardiac stimulator can be implemented to include one or more of the advantageous features or processes described below. It is intended that such a monitor, stimulator, or other implantable or partially implantable device need not include all of the features described herein, but can be implemented to include selected features that provide for unique structures or functionality. Such a device can be implemented to provide a variety of therapeutic or diagnostic functions.

Figure 1:
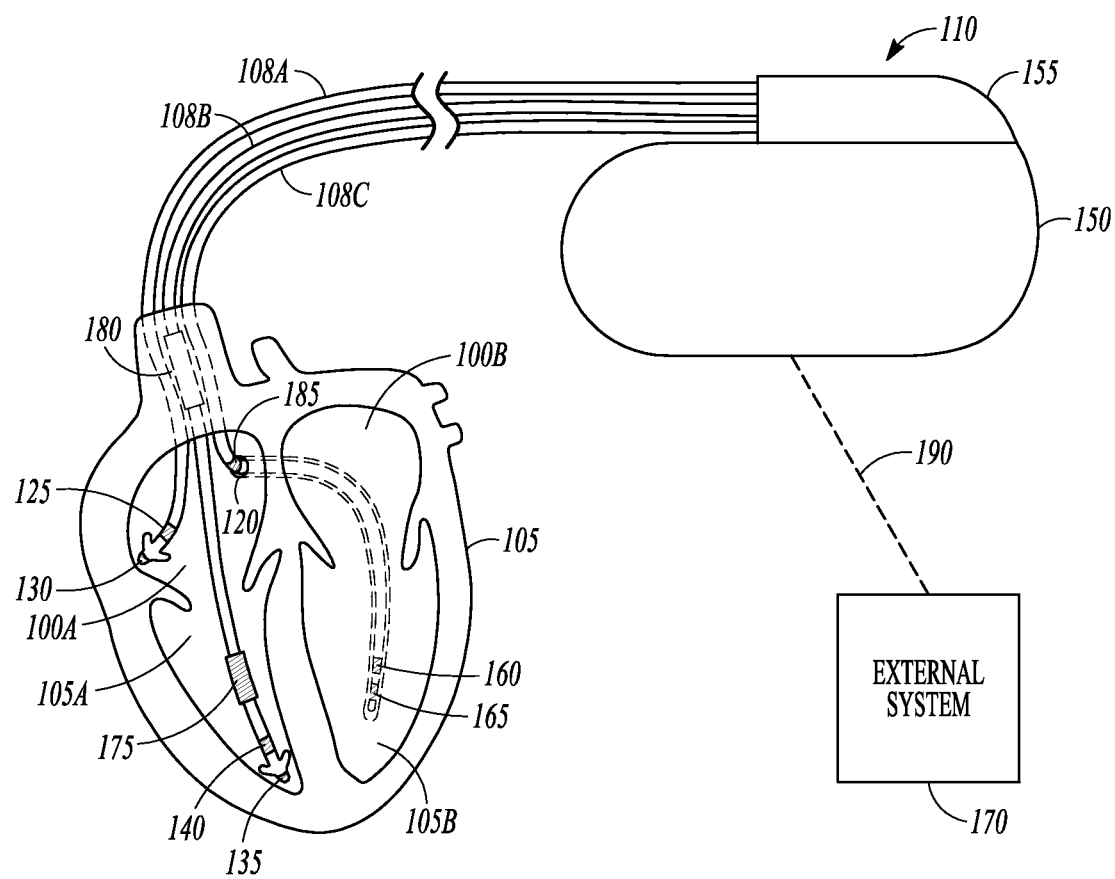
FIG. 1 is an illustration of portions of a system that uses an IMD or other ambulatory medical device.

Medical electronic systems can be used to provide information related to a patient's physiologic condition. FIG. 1 is an illustration of portions of a system that uses an IMD 110 or other ambulatory medical device. Examples of IMD 110 include, without limitation, a pacemaker, a defibrillator, a cardiac resynchronization therapy (CRT) device, a monitoring/diagnostic device, or a combination of such devices. The system also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes can be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation.

The IMD 110 can include a third cardiac lead 108C attached to the IMD 110 through the header 155. The third cardiac lead 108C includes ring electrodes 160 and 165 placed in a coronary vein lying epicardially on the left ventricle (LV) 105B. The third cardiac lead 108C can include a ring electrode 185 positioned near the coronary sinus (CS) 120. Lead 108C optionally provides resynchronization therapy to the heart 105. Resynchronization therapy is typically delivered to the ventricles in order to better synchronize the timing of depolarizations between ventricles.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy can be delivered from the first or RV coil 175 to the second or SVC coil 180. In some examples, the SVC coil 180 can be electrically tied to an electrode formed on the hermetically-sealed IMD housing or can 150. This improves defibrillation by delivering current from the RV coil 175 more uniformly over the ventricular myocardium. In some examples, the therapy can be delivered from the RV coil 175 only to the electrode formed on the IMD can 150.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

Figure 2:
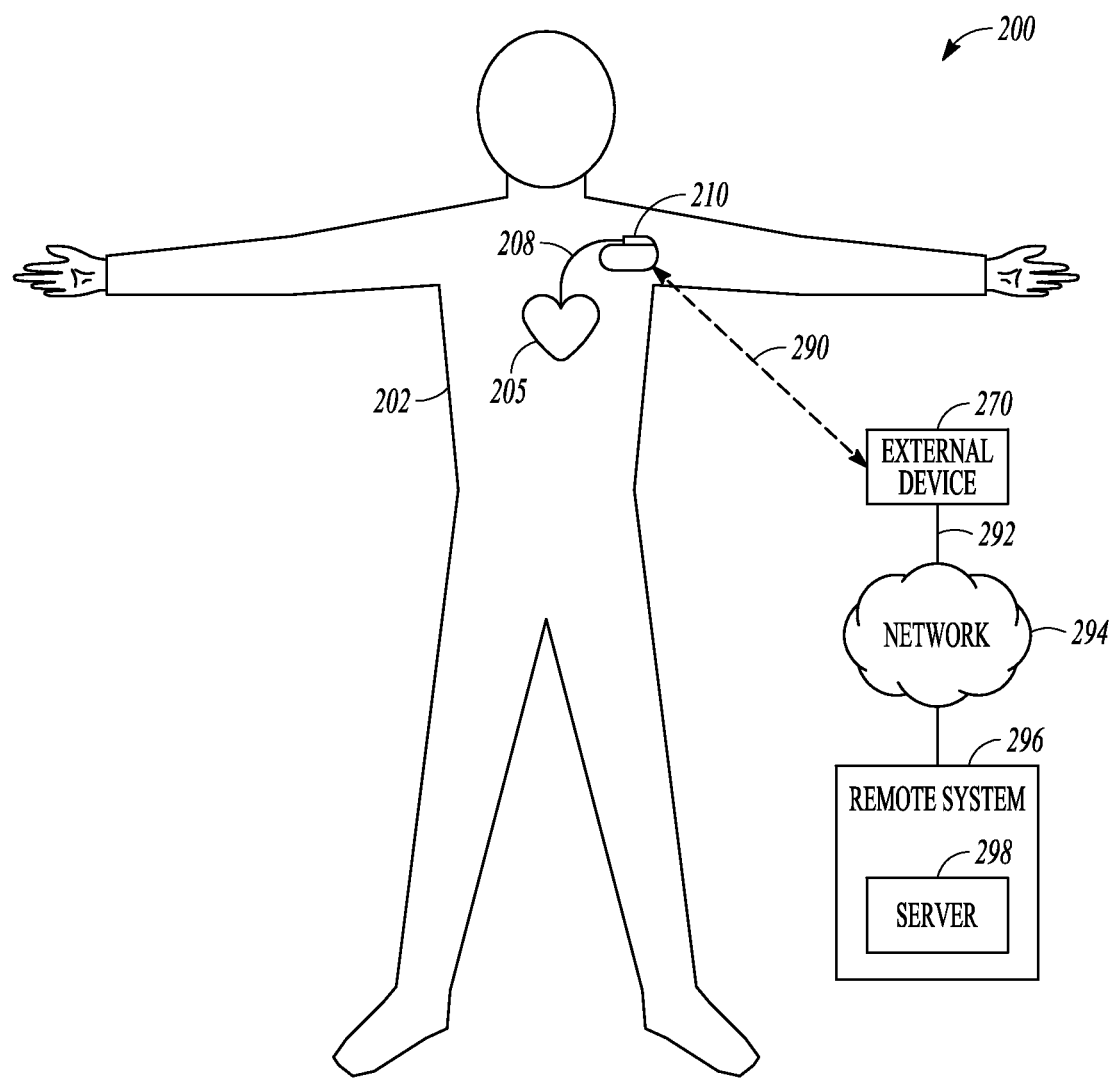
FIG. 2 is an illustration of portions of another system that uses an IMD or other ambulatory medical device.

FIG. 2 is an illustration of portions of another system 200 that uses an IMD or other ambulatory medical device 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicates via the network using a link 292 that can be wired or wireless. In some examples, the remote system 296 provides patient management functions and can include one or more servers 298 to perform the functions.

Many physiologic signals that can be sensed with a medical device or system (e.g., signals related to electrical or mechanical cardiac activity, respiration, heart sounds, and intra-thoracic impedance) can vary due to changes in postural position of the patient as well as changes in cardiac disease.

Figure 3:
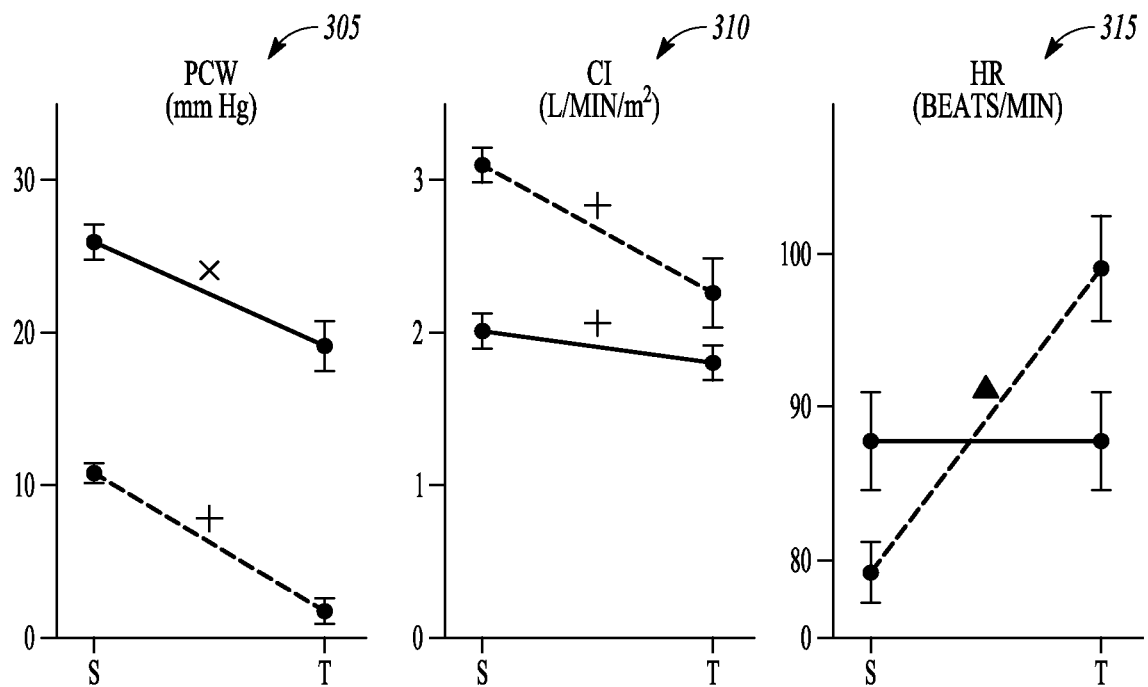
FIG. 3 illustrates example graphs of physiologic measurements.

FIG. 3 illustrates example graphs of physiologic measurements with respect to posture position ('S' for supine and 'T' for tilt). Graph 305 is an example graph of pulmonary capillary wedge (PCW) pressure. PCW can provide an indirect estimate of left atrial pressure. The graph 305 shows that PCW decreases as posture of the patient changes from supine to a tilted posture. The dashed line shows the variation with posture for a patient with a stable heart failure (HF) condition. The solid line shows the variation in PCW with posture for a patient with unstable HF. The graph 305 shows that because the difference between the value of PCW for a supine patient with stable HF and the value for a tilted patient with unstable HF is small, it may be difficult to diagnose the status of HF of the patient using PCW if patient posture is unknown.

Graph 310 is an example graph of cardiac index (CI). CI is a parameter that normalizes cardiac output to body surface area. In other words, a measure of heart performance is related to the size of the patient. The graph 310 shows that CI decreases for a patient with stable HF as posture of the patient changes from supine to tilted, but remains fairly constant as a patient with unstable HF changes posture. The graph shows that because the value of CI for a patient in a tilted posture with stable HF is close to the value of CI for a patient with unstable HF, it may be difficult to diagnose the status of HF of the patient using CI if patient posture is unknown.

Graph 315 is an example graph showing a change in heart rate (HR) as a patient shifts from the supine posture to a tilted posture. Heart rate varies for a patient with stable HF, but stays constant for a patient with unstable HF. Thus, information of posture would allow heart rate to be used in an assessment of HF status of the patient.

The graphs show that when attempting to monitor a physiological signal with a medical device, changes in posture may mask changes in cardiac disease or may lead to false positives for changes in cardiac disease. This variation with posture can be viewed as physiologic noise associated with making physiologic measurements with a medical device. Eliminating physiologic noise from physiologic measurements improves device-based assessments of a subject's health status.

A posture sensor can provide information about posture of a patient or other subject to reduce physiologic noise in device-based measurements. Examples of a posture sensor include a multi-axis accelerometer sensor and a tilt switch.

With a posture sensor, a medical device can detect whether a patient is in an upright position, a recumbent position, a supine position, a prone position, on his or her left or right side, or determine values of the azimuth and tilt angles of subject's posture.

Determining posture with the medical device allows the medical device to compare only those physiologic measurements obtained when a subject is in the same posture. Further, the proper physiologic measurement value for a specific posture may take a few moments to manifest itself in the subject when the subject is changing posture (e.g., from recumbent to upright). Thus, it may be useful to only compare those measurements in which the subject is in a known steady state posture. Using posture information, physiologic measurement values can be categorized or "binned" according to the known postural position, and physiologic measurements for individual posture positions can also be summarized in each bin. This can remove variation of the physiologic measurement that may occur while posture is transient and reduce physiologic noise associated with patient posture.

Figure 4:
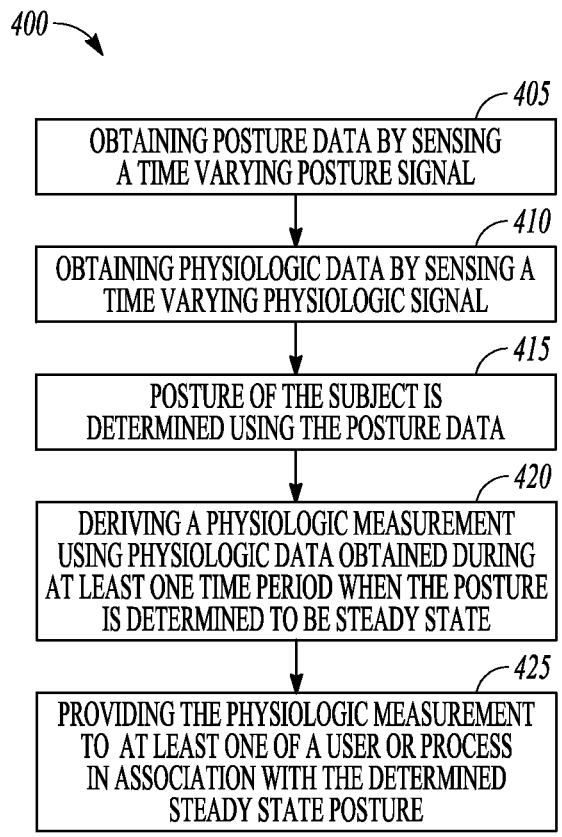
FIG. 4 is a flow diagram of an example of a method of operating an implantable or other ambulatory medical device.

FIG. 4 is a flow diagram of an example of a method 400 of operating an implantable or other ambulatory medical device. At block 405, posture data can be obtained by sensing a time varying posture signal. The posture signal can be obtained from a posture sensor and the posture signal can be representative of posture of a subject.

At block 410, physiologic data can be obtained by sensing a time varying physiologic signal. A physiologic signal includes physiologic information of a subject and can be representative of some aspect of the subject's physiology. Examples of a physiologic signal include, among other things, an intracardiac impedance signal, an intra-thoracic impedance signal, a heart sound signal, a pressure signal, a respiratory frequency or amplitude signal, an accelerometer signal, and a cardiac activity signal.

An intracardiac impedance signal measures impedance across one or more cardiac chambers. To measure a region's impedance, a medical device provides current between cardiac electrodes and measures the resulting voltage using the same or different electrodes. The impedance can be determined by the medical device using Ohm's Law (R=V/I). For instance, an intracardiac impedance signal can be measured between tip electrode 135 and SVC electrode 180 in FIG. 1, or can be measured as a combination of several impedance vectors.

An intra-thoracic impedance signal can be sensed across the thorax region of the subject which can be sometimes called intra-thoracic total impedance (ITTI). For instance, intra-thoracic impedance can be sensed between ring electrode 140 and an electrode formed on the IMD can 150. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference.

A respiration signal includes respiration information about the subject. The respiration signal can include any signal indicative of the respiration of the subject, such as inspiratory volume or flow, expiratory volume or flow, breath rate or timing, or any combination, permutation, or component of the respiration of the subject. A respiration sensor can include an implantable sensor such as one or more of an accelerometer, an impedance sensor, a volume or flow sensor, and a pressure sensor.

Heart sounds are associated with mechanical vibrations from activity of a subject's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the closing of the aortic valve and the beginning of diastole. A heart sound signal is representative of mechanical activity of a patient's heart. The heart sound signal can be provided by a heart sound sensor circuit disposed in a heart, near the heart, or in another location where the acoustic energy of heart sounds can be sensed. In some examples, a heart sound sensor circuit includes an accelerometer disposed in or near a heart. In another example, a heart sound sensor circuit includes an accelerometer disposed in the IMD. In another example, a heart sound sensor circuit includes a microphone disposed in or near a heart.

Many types of physiological information can be included in a signal provided by a heart sound sensor. For example, the presence of an S3 heart sound may be an indication of elevated filling pressure. Thus, the development of, or a change in, an S3 heart sound may indicate a change in status of HF of the subject. An approach for monitoring heart sounds is found in Siejko et al., U.S. Patent Application Publ. No. 2004/0127792, entitled "Method and Apparatus for Monitoring of Diastolic Hemodynamics," filed Dec. 30, 2002, which is incorporated herein by reference in its entirety.

A cardiovascular pressure signal is representative of pressure of a heart chamber or vascular pressure and the signal can be provided by a pressure sensor circuit. An example of a cardiovascular pressure sensor circuit includes a sensor implantable in a coronary vessel to determine left ventricle pressure by direct measurement of coronary vessel pressure. A description of systems and methods that use such an implantable pressure sensor is found in Salo et al., U.S. Pat. No. 6,666,826, entitled "METHOD AND APPARATUS FOR MEASURING LEFT VENTRICULAR PRESSURE," filed Jan. 4, 2002, which is incorporated herein by reference in its entirety. Other cardiovascular pressure sensor examples include a right ventricle (RV) chamber pressure sensor, a pulmonary artery pressure sensor, and a left atrial chamber pressure sensor.

A cardiac activity signal can be representative of electrical activity of the heart such as shifting cardiac tissue membrane potential during a cardiac depolarization. An example of a cardiac signal includes an electrocardiogram (ECG) or electrogram.

At block 415 in FIG. 4, posture of the subject can be determined using the posture data. In some examples, the posture signal can be obtained from a multi-dimensional posture sensor circuit and the signal includes a DC value or near DC value for each of the dimensions. One or more angles of the orientation of the multi-dimensional posture sensor circuit carried by the subject are calculated from the posture signal. The calculated angles can then be compared to specified threshold angles to determine the subject's posture. An approach for determining patient posture using a multi-dimensional posture sensor can be found in Wang et al., "Posture Detector Calibration and Use," U.S. Patent Pub. No. US 2007/0118056, filed Nov. 18, 2005, which is incorporated herein by reference in its entirety. The medical device determines when the posture is steady state (e.g., the subject is in the same posture for 30 seconds or more).

At block 420, a physiologic measurement can be derived using the physiologic data obtained during at least one time period when the posture is determined to be steady state. In some examples, the physiologic signal includes an intrathoracic impedance signal and the physiologic measurement includes a measurement of a parameter related to respiration of the subject. In certain examples, the respiration parameter can be used to determine respiration rate (RR) and the physiologic measurement includes a measurement of RR. In certain examples, the respiration parameter can be used to determine respiration tidal volume (TV), which is the amount of air inhaled and exhaled during each breath cycle of the subject, and the physiologic measurement includes a measure of TV. In certain examples, a measure of TV and RR are used to determine a measure of minute ventilation (MV, which is total volume of air breathed in a minute and is equal to RR×TV) and the physiologic measurement includes a measure of MV.

In some examples, the physiologic signal includes an intra-thoracic impedance signal and the physiologic measurement includes a measurement of cardiac stroke volume. In some examples, the physiologic signal includes a cardiovascular pressure signal and the physiologic measurement may be a measure of left ventricular pressure, right ventricular pressure, pulmonary arterial pressure, and left atrial pressure.

In some examples, the physiologic signal includes a heart sound signal. The physiologic measurement may include a measurement of a heart sound parameter such as, among other things, the presence of an S3 or S4 heart sound, the amplitude of an S1, S2, S3, or S4 heart sound, the duration of a heart sound, or the time of occurrence of a heart sound in relation to another physiologic event (e.g., an R-wave). In some examples, the physiologic signal can be an ECG or electrogram and the physiologic measurement includes a parameter related to an S-wave to T-wave interval, such as the amplitude or the duration of the interval. In some examples, the physiologic signal can be representative of heart rate, such as an R-wave to R-wave interval.

At block 425, the physiologic measurement can be provided to at least one of a user or process in association with the determined steady state posture.

Figure 5:
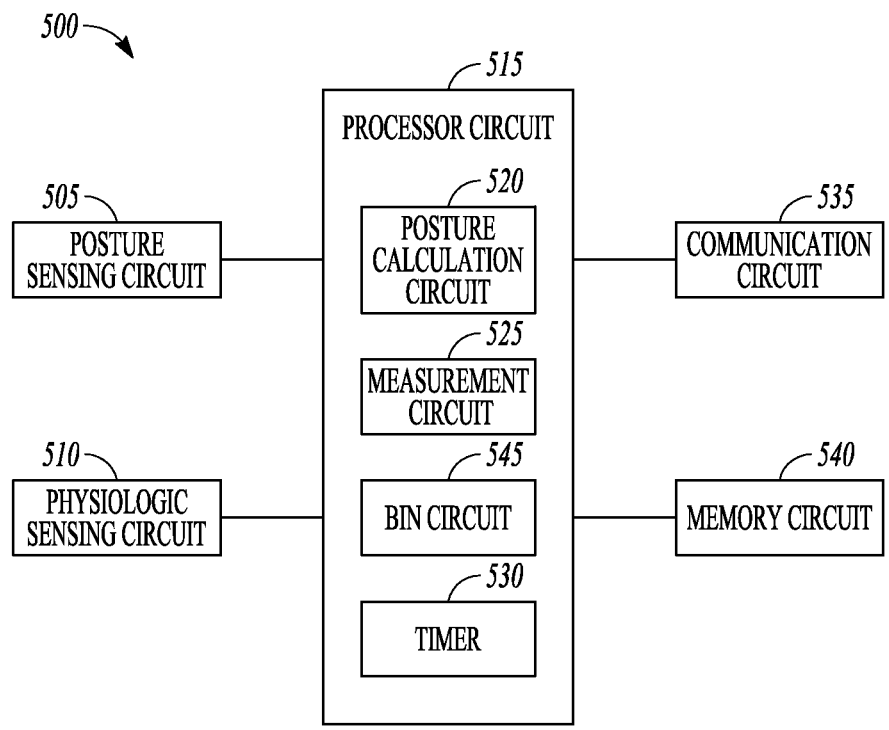
FIG. 5 is block diagram of portions of an example of an implantable or other ambulatory medical device.

FIG. 5 is block diagram of portions of an example of an implantable or other ambulatory medical device 500. The device 500 includes a posture sensing circuit 505 that provides a time varying electrical posture signal representative of posture of a subject. Examples of a posture sensing circuit 505 include a multi-axis accelerometer and a tilt switch. The device 500 also includes a physiologic sensing circuit 510 that senses a time varying physiologic signal from the subject. Some examples of the physiologic sensing circuit 510 include a respiration sensor, a heart sound sensor, an intra-thoracic impedance sensor, a cardiovascular pressure sensor, and a cardiac signal sensing circuit.

The device 500 also includes a processor circuit 515 communicatively coupled to posture sensing circuit 505 and the physiologic sensing circuit 510. The communicative coupling allows electrical signals to be communicated between the sensor circuits and the processor circuit 515 even though there may be one or more intervening circuits between the sensor circuits and the processor circuit 515. For example, the device 500 may include a sampling circuit (not shown) integral to the processor circuit 515 or electrically coupled between the sensor circuits and the processor circuit 515. The sampling circuit can be configured to sample the physiologic signals to produce physiologic data.

The processor circuit 515 can be a microprocessor, a digital signal processor, application specific integrated circuit (ASIC), microprocessor, or other type of processor, interpreting or executing instructions in software modules or firmware modules. The processor circuit 515 includes other circuits or sub-circuits to perform the functions described. These circuits may include software, hardware, firmware or any combination thereof. Multiple functions can be performed in one or more of the circuits as desired.

The processor circuit 515 includes a posture calculation circuit 520 that determines a posture of the subject using posture data obtained using the posture signal and determines when the posture of the subject is steady state. The processor circuit 515 also includes a measurement circuit 525 configured to derive a physiologic measurement using physiologic data extracted from the physiologic signal during at least one time period when posture is determined to be steady state. By limiting the physiologic measurements to time periods when the posture of the subject is steady state, measurement noise from transient posture can be minimized or removed.

According to some examples, steady state posture and the physiologic measurement are determined after the posture data and physiologic data are collected. The device 500 may include a timer circuit 530 integral to or communicatively coupled to the processor circuit 515. The posture calculation circuit 520 obtains the posture data for a specified time duration (e.g., a two hour period) according to the timer circuit 530.

The posture calculation circuit 520 determines a first statistical property of a distribution of the posture data, and determines steady state posture during at least one time period during the specified time duration using the first statistical property.

The posture data collected may include multiple posture angles or posture positions. In some examples, the first statistical property includes a number of modes in the posture data. The posture calculation circuit 520 may detect one or more modes in the data which are the posture angles or positions that occur most frequently in the data. The posture calculation circuit 520 may deem (e.g., generate an indication) that these modes correspond to postures that are steady state. In some examples, the first statistical property includes a mean of the posture data. The posture calculation circuit 520 calculates the mean of the posture data and deems that the calculated mean posture is the steady state posture. In some examples, the first statistical property includes a standard deviation of the posture data. The posture calculation circuit 520 calculates the standard deviation of the posture data. If the standard deviation is small (e.g., less than a specified standard deviation threshold) or if the coefficient of variation is small, the posture calculation circuit 520 may deem that the posture data represents steady state posture.

A device-based threshold, such as the standard deviation threshold, can be pre-specified (e.g., programmed) based on research data or based on a physician preference. In certain examples, a device-based threshold is fixed once it is specified. In certain examples, a device-based threshold can be dynamically redefined during device operation.

In some examples, the first statistical property includes a range of the posture data. The posture calculation circuit 520 determines the range of collected posture data, and if the determined range of posture angles or positions is small (e.g., less than a specified threshold range), the posture calculation circuit 520 may deem that the range corresponds to steady state posture. In some examples, the first statistical property includes a type of posture data distribution. For instance, if the posture calculation circuit 520 detects that the posture data distribution is substantially binomial, the posture calculation circuit may deem that one or both of the postures of the binomial distribution are steady state.

In some examples, the first statistical property includes a percentile of the posture data distribution. The posture calculation circuit may generate an indication that a posture is in steady state when the percentile satisfies (e.g., is above or below) a specified percentile threshold. Other examples of the first statistical property can include a range between two percentiles of the posture data distribution and a standard deviation of the posture data.

The measurement circuit 525 extracts the physiologic data substantially concurrently with the posture data for the specified time duration, regardless of the posture, and derives a second statistical property from the extracted physiologic data as the physiologic measurement. An example of the second statistical property includes a calculated central tendency of the physiologic data, such as a mean or median of the physiologic data. The measurement circuit 525 provides the physiologic measurement to at least one of a user and a process in association with the determined steady state posture.

Figure 6:
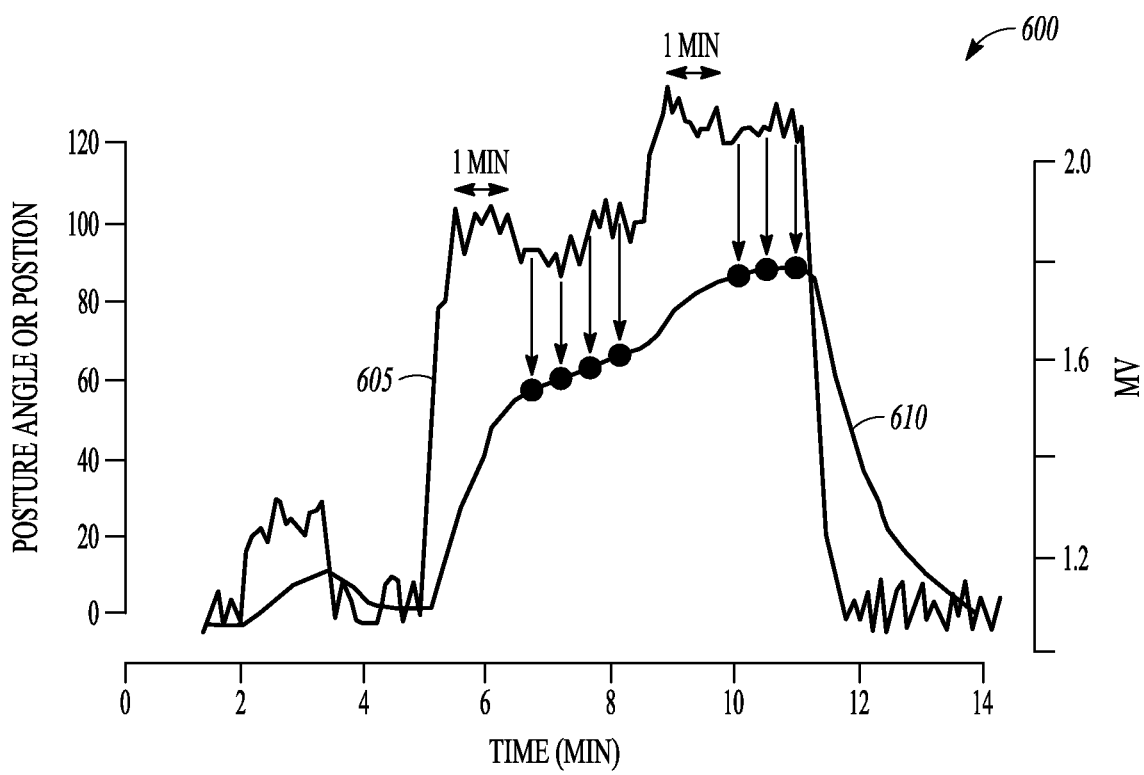
FIG. 6 shows a graph of an example of a posture signal and a physiologic signal representative of minute ventilation.

FIG. 6 shows a graph 600 of an example of a posture signal 605 and a physiologic signal 610 representative of MV. The MV signal may be derived from respiration data. The posture signal 605 and the physiologic signal 610 are collected (e.g., sensed and sampled) for a specified period of time. The posture calculation circuit 520 may determine steady state posture when determining that the posture angle is within a specified standard deviation from five to eight minutes and from nine to eleven minutes. MV for these periods of steady state posture may then be provided to a user or process.

Returning to FIG. 5, in some examples the device 500 includes a memory circuit 540 integral to, or communicatively coupled to, the processor circuit. The measurement circuit 525 can store the physiologic measurement in association with a determined steady state posture. Thus, for the example of FIG. 6, the measurement circuit may store a measurement of MV in association with a determined steady state posture angle (e.g., 0-15°) or position (e.g., supine). In certain examples, the posture calculation circuit can be configured to determine a plurality of postures of the subject and detect steady state for the determined postures, and the measurement circuit can be configured to store a physiologic measurement according to each determined steady state posture. In certain examples, the measurement circuit stores both the physiologic measurement and the determined posture angle or position. Thus, the device 500 can store a measurement of MV for several steady state posture angles or posture positions. In certain examples, a steady state posture can be stored without an associated physiologic measurement.

This information can be stored in the form of a table. An example is shown below in Table 1. In the example, the measurement circuit 525 determines physiologic measurements that include respiration rate, S3 heart sound amplitude, and impedance, for several steady state posture angles. The physiologic measurements are stored for each of the determined steady state posture angles.

TABLE 1

| Mean Tilt Angle (degrees) | Respiration Rate (breaths/minute) | S3 Amplitude (mg) | Intra-thoracic Z (ohms) |
| --- | --- | --- | --- |
| 0-15 | 30 | 5 | 22 |
| 16-30 | 25 | 3 | 24 |
| 31-45 | 20 | 2 | 27 |
| ... | ... | ... | ... |

It is possible that the device may not find a steady state posture during the specified time period. For example, the distribution of the posture data may be uniform, possibly indicating that the subject did not have a steady state posture during the two hour period or that the posture sensing circuit 505 was unable to detect a steady state posture during the period. In this case, the amount of posture noise is high and the measurement circuit 525 may not store any physiologic measurements for the time period.

In some examples, the device 500 is an ambulatory device and includes a display. The processor circuit 515 may execute a process to display the information (e.g., in a table) to a user on the display. In some examples, the device 500 is an implantable device and communicates wirelessly with a second device using a communication circuit 535, such as by RF or inductive telemetry. The second device may have a display to present the information to a user.

Additional information may be stored in association with steady state posture. For example, the posture calculation circuit 520 may determine the time duration that the posture is in steady state and store the time duration in association with the physiologic measurement and the determined steady state posture.

Other examples of presenting posture information are shown below in Table 2. In the first row, types of positions or postures are determined for the subject. A histogram bin can be created in the memory circuit 540 for each determined posture. The amount of time or percentage of time the subject spends in each posture can be stored in association with the bins.

TABLE 2

| Posture Signal | Histogram Bin Type | Histogram y-value |
| --- | --- | --- |
| Position types (e.g., supine) | All Possible Position Types | % of Time Period Spent in a Given Position Type |
| Numerical Values Representing Certain Tilt Angle | Degrees (e.g., 0 to 180 degrees, bin size = 15 degrees) | % of Time Period Spent at Angles Spanned by Given Bin |
| Combination of Several Tilt Angles (e.g., continuous version of position type) | Numerical Ranges for Each Angle Spilt into Bins, Forming a Multi-dimensional Histogram | % of Time Period Spent at Combinations Spanned by Given Multi-dimensional Bin |

In the middle row of the Table, steady state posture angle is calculated and histogram bins are created for a specified range of angles (e.g., 0°-15°, 16°-30°, etc,). The percentage time the subject spends in the range of each bin can be stored in association with the bins. In the bottom row, ranges of posture angles are defined for several posture positions. Histogram bins are formed for the ranges.

In some examples, the device 500 generates a table of information for each data collecting period (e.g., the two hour period) of collecting data. In some examples, the device 500 generates a table according to a specified schedule (e.g., once a day).

Figure 7:
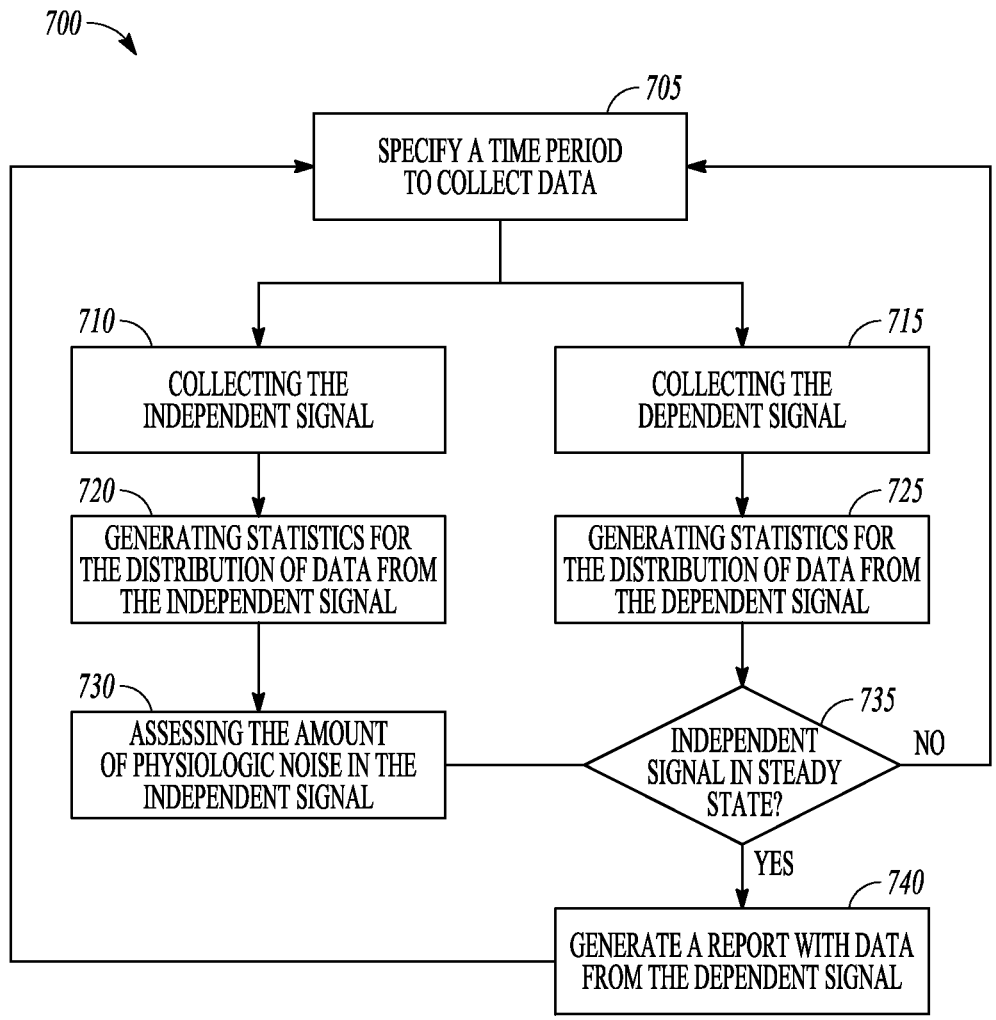
FIG. 7 shows a flow diagram of an example of a method of extracting a physiologic measurement from a dependent signal during a period when the independent signal is determined to be steady state.

This method can be generalized beyond taking measurements based on steady state posture. FIG. 7 shows a flow diagram of this method 700 of extracting a physiologic measurement from a dependent signal during a period when the driving or independent signal is determined to be steady state. At block 705 a time period is specified to collect data. At block 710, data for the independent signal can be collected. Examples of an independent signal include a posture signal, or another sensed or derived signal (e.g., subject activity, heart rate, MV, or ITTI). At block 715, data for a dependent physiologic signal can be collected during the time period. The signal can be dependent because the value of this data can depend on what is happening on the independent signal. Typically, the data from the independent signal and the dependent signal are collected at substantially the same time.

At block 720, one or more statistics are generated for the distribution of the data collected using the independent signal. Some examples include a measure central tendency of the data (mean, median), standard deviation, a number of modes in the data, a type of data distribution, a range of the data, a percentile of the data distribution, and a range between two percentiles of the data distribution. At block 725, one or more statistics are generated for the distribution of data collected using the dependent signal.

At block 730, the amount of physiologic noise (e.g., posture noise, respiration noise, etc.) from the independent signal can be assessed. The assessment can be based on the statistics generated for the independent signal. For instance, if the data distribution for the independent signal is uniform for the specified time period, the device 500 assesses that the amount of noise is high. At block 735, it can be determined whether any steady state data is available for the time period based on the generated statistics. If the statistics indicate that the independent signal was not steady state during the time period, flow continues to back to block 705 to wait for the next data collecting period and the device may not store physiologic measurements determined from the dependent signal during this time period or may not generate a table of information for the time period. If the assessment is that little noise is present (e.g., the generated statistics indicate at least some durations of steady state during the time period), a table or report can be generated for the time period at block 740 and flow then returns to block 705 to wait for the next data collecting time period.

In the example of FIG. 5, the independent signal is a posture signal. Other signals may be used as the independent signal. For instance, the device 500 may include a respiration sensing circuit, configured to provide a time varying electrical respiration signal representative of respiration of a subject, instead of a posture sensing circuit. Some examples of a respiration sensing circuit include a respiration sensor and an intra-thoracic impedance sensor.

The physiologic sensing circuit 510 provides the dependent physiologic signal and can include at least one of a heart sound sensor, a cardiovascular pressure sensor, and a cardiac signal sensing circuit.

The processor circuit 515 includes an MV circuit (instead of a posture calculation circuit) to determine MV of the subject using respiration data obtained using the respiration signal and to determine when MV of the subject is steady state. To detect steady state MV, the MV circuit collects respiration data for the specified time duration and determines a first statistical property of a distribution of the respiration data. The MV circuit determines steady state MV during at least one time period during the specified time duration using the statistical property.

The measurement circuit 525 extracts physiologic data substantially concurrently with the respiration data for the specified time duration. The measurement circuit 525 derives a second statistical property for the physiologic parameter from the extracted physiologic data during at least one duration of time when MV is determined to be steady state and provides the measurement of the physiologic parameter to at least one of a user and a process in association with the determined steady state MV.

In some examples, physiologic measurements are stored in association with different values of steady state MV. In some examples, the information can be presented to a user in a table (e.g., measurements of the amplitude of the S3 heart sound and measurements of cardiovascular pressure for different values of steady state MV).

According to some examples, instead of collecting physiologic data and posture data simultaneously, physiologic data is not collected until the device determines that the posture is steady state. Returning to the example where the device 500 includes a posture sensing circuit 505, a first time period is defined that begins when the posture calculation circuit 520 determines that posture is steady state and ends when the posture calculation circuit 520 determines that posture is no longer steady state.

The processor circuit 515 stores physiologic data for the first time period. The measurement circuit 525 may derive a first value for the physiologic measurement from the physiologic data stored during the first time period. In certain examples, the physiologic measurement can be calculated when steady state posture is detected. The processor circuit 515 defines a second time period that begins when the posture calculation circuit 520 determines that posture is again steady state and ends when the posture calculation circuit 520 determines that posture is no longer steady state. The measurement circuit 525 derives a second value for the physiologic measurement from the physiologic data stored during the second time period.

In some examples, the first and second values of the physiologic measurement are stored in memory circuit 540 and are reported later when data is retrieved from the device. In some examples, the measurement circuit 525 determines a composite value of the physiologic measurement using the first second derived values (e.g., a central tendency of the first and second derived values).

According to some examples, the device 500 determines steady state posture by binning posture data. In certain examples, the posture calculation circuit 520 collects posture data continuously, such as by sampling the posture data at a specified rate (e.g., eight samples per minute), over a specified period of time (e.g., twenty-four hours). The posture calculation circuit 520 includes a bin circuit 545 that calculates a bin number of posture data using an average calculated from N samples of posture data, where N is an integer. In certain examples, the N samples are sequential samples.

In some examples, the posture bin number is a ratio of calculated average to a specified bin size with any remainder being truncated. The bin size can be specified of chosen according to range of values the posture sensing circuit 505 can output and the number of bins desired. As an illustrative example, if the output from the posture sensing circuit 505 is a posture angle that varies from 0° to 180° and 12 bins are desired, the bin size can be 15°. In some examples, raw data from the posture sensing circuit 505 rather than determined posture angles can be binned and used to the bin size. If the calculated average of the N samples is 30°, the posture bin number for the average is 30/15, or 2. The posture bin number would also be 2 for calculated averages of 31°-54°.

In some examples, the posture calculation circuit 520 determines a running buffer of M calculated bin number values, where M is an integer. In some examples, the memory circuit 540 can be configured to include a first-in first-out (FIFO) as the running buffer.

The posture calculation circuit 520 uses the running buffer of calculated bin numbers to determine steady state posture of the subject. The posture calculation circuit 520 identifies or obtains the most current calculated bin number. In certain examples, the posture calculation circuit 520 may deem the posture of the subject be out of steady state when the current bin number differs from its previous bin number in the running buffer by more than a first specified bin number threshold value (e.g., the current bin number differs by more than P bins from the most recent of the M bins in the running buffer).

In certain examples, the posture calculation circuit 520 may deem the posture of the subject to be out of steady state when the current bin number differs from any pair of previous Mbin numbers by more than a second specified bin number threshold value. (E.g., the current bin number is more than Q bins different from any pair of the previous M bins in the running buffer. In an example, P and Q are integers and P=Q/2.) In certain examples, the posture calculation circuit 520 may deem the posture of the subject to be out of steady state when bin number values in the running buffer are steadily increasing or decreasing. In certain examples, the posture calculation circuit 520 identifies the center value of the running buffer as the current bin number and uses the M/2 values after the current bin number as a look-ahead buffer. The posture calculation circuit 520 may deem the posture of the subject to be out of steady state when the M/2 bin number values in the first half of the running buffer and the M/2 bin number values in the look ahead portion of the running buffer are steadily increasing or decreasing.

In certain examples, the posture calculation circuit 520 may deem that the posture of the subject is out of steady state when any one of i) the current bin number differs from its previous bin number in the running buffer by more than a first specified bin number threshold value, ii) the current bin number differs from any pair of previous M bin numbers by more than a second specified bin number threshold value, and iii) bin number values in the running buffer are steadily increasing or decreasing, otherwise deem the posture to be steady state.

When the posture is determined to be steady state physiologic data is added to the same or a different running buffer in the device 500. Physiologic data is accumulated while the posture data is determined to be steady state using the test or tests for steady state posture. In some examples, when the posture data fails the test for steady state after previously passing the test for steady state posture, the buffered physiologic data is summarized (e.g., a mean, median, or other statistical property is calculated for the data), and the summarized data can be stored by posture bin.

When the time period for monitoring posture and the physiology data (e.g., the twenty-four hour period) has expired, physiologic data for the time period can be summarized. The summarized data can be displayed as a table on a wearable medical device or communicated from an implantable device for display on a second device. In certain examples, such a table can include bin number, posture range or posture position for the bin number, the summarized physiologic data corresponding to the bin number, and the amount of time the subject was steady state in the posture corresponding to the bin number. In certain examples, the data can be presented through statistical tests such as linear or quadratic regression of the physiologic data versus either bin number or posture position. The summarized physiologic data can include, among other things, a calculated summary of PCW, cardiac index, heart rate, respiration rate, ITTI, MV, TV, cardiac stroke volume, and one or more measured heart sound parameters.

According to some examples, the device 500 includes an activity sensing circuit in addition to the posture sensing circuit 505 and the physiologic sensing circuit 510. An example of an activity sensing circuit includes an accelerometer. The activity sensing circuit provides a time varying electrical activity signal representative of activity of a subject. The processor circuit 515 includes an activity detection circuit configured to determine when activity of the subject is steady state. In some examples, the activity detection circuit deems the posture is not steady state when determining that the posture signal provided by the posture sensor varies by more than a specified posture signal variation threshold for a specified time duration. In some examples, the activity detection circuit determines steady state activity by binning activity data and using one or more of the steady state tests described previously.

The measurement circuit 525 measures the physiologic parameter using physiologic data obtained during at least one time period when both activity of the subject is determined to be steady state and the posture of the subject is determined to be steady state. In this way, the device 500 can remove physiologic noise due to activity of the subject and due to changes in posture of the subject in order to better monitor the subject's cardiac disease.

ADDITIONAL NOTES

Example 1 includes subject matter, such as an implantable or other ambulatory medical apparatus, comprising a posture sensing circuit configured to provide a time varying electrical posture signal representative of posture of a subject, a physiologic sensing circuit configured to sense one or more time varying physiologic signals, and a processor circuit communicatively coupled to the posture sensing circuit and the physiologic sensing circuit. The physiologic signal includes physiologic information of the subject. The processor circuit includes a posture calculation circuit configured to determine a posture of the subject using posture data obtained using the posture signal and determine when the posture of the subject is steady state, and a measurement circuit configured to derive a physiologic measurement using physiologic data extracted from the physiologic signal during at least one time period when posture is determined to be steady state, and provide the physiologic measurement to at least one of a user and a process in association with the determined steady state posture.

In Example 2, the physiologic sensing circuit of Example 1 can optionally include at least one of a respiration sensor, a heart sound sensor, an impedance sensor, a cardiovascular pressure sensor, and a cardiac signal sensing circuit.

In Example 3, the physiologic measurement of one or any combination of Examples 1 and 2 can optionally include a measurement of at least one of minute ventilation, cardiovascular pressure, a respiration parameter, a heart sound parameter, an impedance parameter, and a parameter related to an S-wave to T-wave interval.

In Example 4, the subject matter of one or any combination of Examples 1-3 can optionally include a timer circuit integral to or communicatively coupled to the processor circuit. The posture calculation circuit can optionally be configured to obtain the posture data for a specified time duration, determine a first statistical property of a distribution of the posture data, and determine steady state posture during at least one time period during the specified time duration using the first statistical property. The measurement circuit can optionally be configured to extract the physiologic data substantially concurrently with the posture data for the specified time duration, and derive a second statistical property from the extracted physiologic data as the physiologic measurement.

In Example 5, the posture calculation circuit of one or any combination of Examples 1-4 can optionally be configured to determine, as the first statistical property for the distribution of the posture data, at least one of: a number of posture modes in the posture data, a type of posture data distribution, a mean of the posture data, a range of the posture data, a percentile of the posture data distribution, a range between two percentiles of the posture data distribution, and a standard deviation of the posture data.

In Example 6, the subject matter of one or any combination of Examples 1-5 can optionally include a memory integral to, or communicatively coupled to, the processor circuit. The processor circuit can optionally be configured to store physiologic data for a first time period that begins when it is determined that posture is steady state and ends when it is determined that posture is no longer steady state, and store physiologic data for a second time period that begins when it is determined that posture is again steady state and ends when it is determined that posture is no longer steady state. The measurement circuit can optionally be configured to derive a first value for the physiologic measurement from the physiologic data stored during the first time period, derive a second value for the physiologic measurement from the physiologic data stored during the second time period, and determine a composite value of the physiologic measurement using the first and second derived values.

In Example 7, the subject matter of one or any combination of Examples 1-6 can optionally include a sampling circuit communicatively coupled to the posture sensing circuit and the processor circuit and configured to sample the posture signal to obtain the posture data. The posture calculation circuit can optionally include a bin circuit configured to calculate a bin number of posture data using a metric calculated from N samples of posture data, wherein N is an integer greater than or equal to one, determine a running buffer of Mbin numbers, wherein each bin number is calculated from N samples, wherein M is an integer, and determine steady state posture using the running buffer of calculated bin number values.

In Example 8 the posture calculation circuit of one or any combination of Examples 1-7 can optionally be configured to obtain a current bin number, and deem (e.g., generate an indication) the posture to be out of steady state when determining at least one of: the current bin number differs from its previous bin number by more than a first specified bin number threshold value, the current bin number differs from any pair of previous Mbin numbers by more than a second specified bin number threshold value, and bin number values in the running buffer are steadily increasing or decreasing, and otherwise deem the posture to be steady state.

In Example 9, the subject matter of one or any combination of Examples 1-8 can optionally include an activity sensing circuit configured to provide a time varying electrical activity signal representative of activity of a subject. The processor circuit can optionally include an activity detection circuit configured to determine when activity of the subject is steady state. The measurement circuit can optionally be configured to measure the physiologic parameter using physiologic data obtained during at least one time period when activity of the subject is determined to be steady state and the posture of the subject is determined to be steady state.

In Example 10, the subject matter of one or any combination of Examples 1-9 can optionally include a memory circuit integral to, or communicatively coupled to, the processor circuit. The measurement circuit can optionally be configured to store the physiologic measurement in association with a determined steady state posture.

In Example 11, the posture calculation circuit of one or any combination of Examples 1-10 can optionally be configured to determine a plurality of postures of the subject and detect steady state for the determined postures. The measurement circuit can optionally be configured to store at least one of a determined posture and a physiologic measurement according to each determined steady state posture.

In Example 12, the subject matter of one or any combination of Examples 1-11 can optionally include a timer circuit integral to or communicatively coupled to the processor circuit. The posture calculation circuit can optionally be configured to determine a time duration that the posture is in steady state and store the time duration in association with the physiologic measurement and the determined steady state posture.

Example 13 can include subject matter, or can optionally be combined with the subject matter of one or any combination of Examples 1-12 to include subject matter (such as an implantable or other ambulatory medical apparatus), comprising a respiration sensing circuit configured to provide a time varying electrical respiration signal representative of respiration of a subject, a physiologic sensing circuit to sense a time varying physiologic signal from the subject, and a processor circuit communicatively coupled to the respiration sensing circuit and the physiologic sensing circuit. The physiologic signal provides physiologic information of the subject. The processor circuit includes an MV circuit configured to determine MV of the subject using respiration data obtained using the respiration signal and determine when MV of the subject is steady state, and includes a measurement circuit configured to measure a physiologic parameter using physiologic data extracted from the physiologic signal during at least one time period when MV is determined to be steady state, and provide the measurement of the physiologic parameter to at least one of a user and a process in association with the determined steady state MV.

In Example 14, the respiration sensing circuit of Example 13 optionally includes at least one of a respiration sensor and an intra-thoracic impedance sensor. The physiologic sensing circuit can optionally include at least one of a heart sound sensor, a cardiovascular pressure sensor, and a cardiac signal sensing circuit.

In Example 15, the subject matter of one or any combination of Examples 13 and 14 can optionally include a timer circuit integral to or communicatively coupled to the processor circuit. The MV circuit can optionally be configured to obtain the respiration data for a specified time duration, determine a first statistical property of a distribution of the respiration data, and determine steady state MV during at least one time period during the specified time duration using the statistical property. The measurement circuit can optionally be configured to extract the physiologic data substantially concurrently with the respiration data for the specified time duration and derive a second statistical property for the physiologic parameter from the extracted physiologic data.

In Example 16, the subject matter of one or any combination of Examples 13-15 can optionally be include a memory circuit integral to, or communicatively coupled to, the processor circuit. The processor circuit can optionally be configured to store physiologic data for a first time period, wherein the first time period begins when it is determined that MV is steady state and ends when it is determined that MV is no longer steady state and store physiologic data for a second time period, wherein the second time period begins when it is determined that MV is again steady state and ends when it is determined that MV is no longer steady state. The measurement circuit can optionally be configured to derive a first composite value for the physiologic parameter from the physiologic data stored during the first time period, derive a second composite value for the physiologic parameter from the physiologic data stored during the second time period, and determine the measure of the physiologic parameter using the first composite value and the second composite value.

Example 17 can include subject matter, or can optionally be combined with the subject matter of one or any combination of Examples 1-16 to include subject matter, (such as a method, a means for performing acts, or a machine-readable medium containing instructions that, when performed by the machine, cause the machine to perform acts), comprising obtaining posture data by sensing a time varying posture signal, wherein the posture signal is representative of posture of a subject, obtaining physiologic data by sensing a time varying physiologic signal, wherein the physiologic signal includes physiologic information of the subject, determining posture of the subject using the posture data, deriving a physiologic measurement using physiologic data obtained during at least one time period when the posture is determined to be steady state, and providing the physiologic measurement to at least one of a user or process in association with the determined steady state posture.

In Example 18, the physiologic measurement of Example 17 can optionally include a measurement of at least one of a respiration parameter, a heart sound parameter, minute ventilation, cardiovascular pressure, and a parameter related to an S-wave to T-wave interval.

In Example 19 the determining posture of one or any combination of Examples 17 and 18 can optionally include obtaining the posture data for a specified time duration, determining a first statistical property of a distribution of the posture data, and determining steady state posture during at least one time period during the specified time duration using the statistical property. The obtaining physiologic data can optionally include obtaining the physiologic data substantially concurrently with the posture data for the specified time duration and deriving a physiologic measurement using the physiologic data includes deriving a second statistical property from the physiologic data.

In Example 20, the obtaining the physiologic data of one or any combination of Examples 17-19 can optionally include storing the physiologic data for a first time period, wherein the time period begins when determining that posture is steady state and ends when determining that posture is no longer steady state, and storing the physiologic data for a second time period, wherein the time period begins when determining that posture returns to steady state and ends when determining that posture is no longer steady state. The deriving a physiologic measurement can optionally include deriving a first value of the physiologic measurement from the physiologic data stored during the first time period, deriving a second value of the physiologic measurement from the physiologic data stored during the second time period, and determining a composite value of the physiologic measurement using the first and second derived values.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

The above non-limiting Examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable or other ambulatory medical apparatus comprising:
a posture sensing circuit configured to provide a time varying electrical posture signal representative of posture of a subject;
a physiologic sensing circuit configured to sense one or more time varying physiologic signals, wherein the physiologic signal includes physiologic information of the subject; and
a processor circuit, communicatively coupled to the posture sensing circuit and the physiologic sensing circuit, wherein the processor circuit includes:
a posture calculation circuit configured to determine a posture of the subject and that the posture of the subject is steady state using posture data obtained using the posture signal; and
a measurement circuit configured to derive a physiologic measurement indicative of heart failure (HF) status of the subject using physiologic data extracted from the physiologic signal, wherein the physiologic measurement is triggered by the posture calculation circuit determining that posture is steady state; and
a memory circuit, wherein the processor circuit is configured to store the physiologic measurement indicative of HF status in association with the determined corresponding steady state posture in response to the posture calculation circuit determining that posture is steady state, wherein the corresponding posture is substantially the same for the stored physiological measurement indicative of HF status and level of activity of the subject varies for the stored physiological measurement indicative of HF status, and provide the physiologic measurement indicative of HF status to at least one of a user or process in association with the determined corresponding steady state posture.

2. The apparatus of claim 1, wherein the physiologic sensing circuit includes at least one of a respiration sensor, a heart sound sensor, an impedance sensor, a cardiovascular pressure sensor, and a cardiac signal sensing circuit.

3. The apparatus of claim 1, wherein the physiologic measurement includes a measurement of at least one of minute ventilation, cardiovascular pressure, a respiration parameter, a heart sound parameter, an impedance parameter, and a parameter related to an S-wave to T-wave interval.

4. The apparatus of claim 1, including:
a timer circuit integral to or communicatively coupled to the processor circuit;
wherein the posture calculation circuit is configured to:
obtain the posture data for a specified time duration;
determine a first statistical property of a distribution of the posture data; and
determine steady state posture during at least one time period during the specified time duration using the first statistical property; and wherein the measurement circuit is configured to:
extract the physiologic data substantially concurrently with the posture data for the specified time duration; and
derive a second statistical property from the extracted physiologic data as the physiologic measurement.

5. The apparatus of claim 4, wherein the posture calculation circuit is configured to determine, as the first statistical property for the distribution of the posture data, at least one of:
a number of posture modes in the posture data;
a type of posture data distribution;
a mean of the posture data;
a range of the posture data;
a percentile of the posture data distribution;
a range between two percentiles of the posture data distribution; and
a standard deviation of the posture data.

6. The apparatus of claim 1, including:
a memory integral to, or communicatively coupled to, the processor circuit;
wherein the processor circuit is configured to:
store physiologic data for a first time period, wherein the first time period begins when it is determined that posture is steady state and ends when it is determined that posture is no longer steady state; and
store physiologic data for a second time period, wherein the second time period begins when it is determined that posture is again steady state and ends when it is determined that posture is no longer steady state; and
wherein the measurement circuit is configured to:
derive a first value for the physiologic measurement from the physiologic data stored during the first time period;
derive a second value for the physiologic measurement from the physiologic data stored during the second time period; and
determine a composite value of the physiologic measurement using the first and second derived values.

7. The apparatus of claim 6, including:
a sampling circuit, communicatively coupled to the posture sensing circuit and the processor circuit, configured to sample the posture signal to obtain the posture data;
wherein the posture calculation circuit includes a bin circuit configured to:
calculate a bin number of posture data using a metric calculated from N samples of posture data, wherein N is an integer greater than or equal to one;
determine a running buffer of M bin numbers, wherein each bin number is calculated from N samples, wherein M is an integer; and
determine steady state posture using the running buffer of calculated bin number values.

8. The apparatus of claim 7, wherein the posture calculation circuit is configured to:
obtain a current bin number;
deem the posture to be out of steady state when determining at least one of:
the current bin number differs from its previous bin number by more than a first specified bin number threshold value;
the current bin number differs from any pair of previous M bin numbers by more than a second specified bin number threshold value; and bin number values in the running buffer are steadily increasing or decreasing; and otherwise deem the posture to be steady state.

9. The apparatus of claim 1, including:

an activity sensing circuit configured to provide a time varying electrical activity signal representative of activity of a subject, wherein the processor circuit includes an activity detection circuit configured to determine when activity of the subject is steady state, and wherein the measurement circuit is configured to measure the physiologic parameter using physiologic data obtained during at least one time period when activity of the subject is determined to be steady state and the posture of the subject is determined to be steady state.

10. The apparatus of claim 1, including:

a memory circuit integral to, or communicatively coupled to, the processor circuit, wherein the measurement circuit is configured to store the physiologic measurement in association with a determined steady state posture.

11. The apparatus of claim 10, wherein the posture calculation circuit is configured to determine a plurality of postures of the subject and detect steady state for the determined postures, and wherein the measurement circuit is configured to store at least one of a determined posture and a physiologic measurement according to each determined steady state posture.

12. The apparatus of claim 10, including:

a timer circuit integral to or communicatively coupled to the processor circuit, wherein the posture calculation circuit is configured to determine a time duration that the posture is in steady state and store the time duration in association with the physiologic measurement and the determined steady state posture.

13. A method of operating an implantable or other ambulatory medical device comprising:

obtaining posture data by sensing a time varying posture signal, wherein the posture signal is representative of posture of a subject;

obtaining physiologic data by sensing a time varying physiologic signal, wherein the physiologic signal includes physiologic information of the subject;

determining a posture of the subject and determining that the posture is steady state using the posture data;

initiating, in response to a device-determination that the posture is steady state, a physiologic measurement indicative of heart failure (HF) status of the subject using the obtained physiologic data posture;

storing, in response to the determination that the posture is steady state, the physiologic measurement indicative of HF status in association with the corresponding device-determined steady state posture, wherein the corresponding posture is substantially the same for the stored physiological measurement indicative of HF status and level of activity of the subject varies for the stored physiological measurement indicative of HF status; and providing the device-derived physiologic measurement to at least one of a user or process in association with the determined corresponding steady state posture.

14. The method of claim 13, wherein the physiologic measurement includes a measurement of at least one of a respiration parameter, a heart sound parameter, minute ventilation, cardiovascular pressure, and a parameter related to an S-wave to T-wave interval.

15. The method of claim 13, wherein determining posture includes:

obtaining the posture data for a specified time duration;

determining a first statistical property of a distribution of the posture data; and determining steady state posture during at least one time period during the specified time duration using the statistical property; and wherein obtaining physiologic data includes obtaining the physiologic data substantially concurrently with the posture data for the specified time duration; and deriving a physiologic measurement using the physiologic data includes deriving a second statistical property from the physiologic data.

16. The method of claim 13, wherein obtaining the physiologic data includes:

storing the physiologic data for a first time period, wherein the time period begins when determining that posture is steady state and ends when determining that posture is no longer steady state; and storing the physiologic data for a second time period, wherein the time period begins when determining that posture returns to steady state and ends when determining that posture is no longer steady state; and wherein deriving a physiologic measurement includes:

deriving a first value of the physiologic measurement from the physiologic data stored during the first time period;

deriving a second value of the physiologic measurement from the physiologic data stored during the second time period; and determining a composite value of the physiologic measurement using the first and second derived values.

* * * * *